(12) United States Patent
Zhang et al.

(10) Patent No.: US 9,173,918 B2
(45) Date of Patent: Nov. 3, 2015

(54) COMPOSITIONS AND METHODS FOR THE TREATMENT OF CARDIAC SURGERY-ASSOCIATED ACUTE KIDNEY INJURY WITH ANNEXIN A1 PEPTIDE

(75) Inventors: Zhiquan Zhang, Durham, NC (US); G. Burkhard Mackensen, Durham, NC (US); Qing Ma, Durham, NC (US); Mihai V. Podgoreanu, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/879,558

(22) PCT Filed: Oct. 14, 2011

(86) PCT No.: PCT/US2011/056400
§ 371 (c)(1),
(2), (4) Date: Sep. 3, 2013

(87) PCT Pub. No.: WO2012/051556
PCT Pub. Date: Apr. 19, 2012

(65) Prior Publication Data
US 2014/0296149 A1    Oct. 2, 2014

Related U.S. Application Data

(60) Provisional application No. 61/393,402, filed on Oct. 15, 2010.

(51) Int. Cl.
*A61K 38/06*    (2006.01)
*C07K 5/08*    (2006.01)
*A61P 13/12*    (2006.01)
*A61K 38/07*    (2006.01)
*A61K 38/17*    (2006.01)

(52) U.S. Cl.
CPC ............. *A61K 38/07* (2013.01); *A61K 38/1709* (2013.01)

(58) Field of Classification Search
CPC .......................... A61K 38/07; A61K 38/1709
See application file for complete search history.

(56) References Cited

U.S. PATENT DOCUMENTS

| | | | |
|---|---|---|---|
| 5,849,502 | A | 12/1998 | Tsao |
| 2003/0171297 | A1 | 9/2003 | Perritti et al. |
| 2006/0024315 | A1 | 2/2006 | Schnitzer et al. |
| 2007/0124086 | A1 | 5/2007 | Mendrick et al. |
| 2010/0203512 | A1 | 8/2010 | Chen et al. |
| 2012/0004175 | A1 | 1/2012 | Zhang et al. |
| 2012/0270790 | A1 | 10/2012 | Podgoreanu et al. |

FOREIGN PATENT DOCUMENTS

WO    WO 2008/121881 A2    10/2008

OTHER PUBLICATIONS

Sheridan et al, Cell biology and molecular mechanisms of injury in ischemic acute renal failure, Curr Opin Nephrol Hypertens, 2000, 9, pp. 427-434.*
Devarajan, Update on Mechanisms of Ischemic Acute Kidney Injury, J Am Soc Nephrol, 2006, 17, pp. 1503-1520.*
Cao et al, In vivo transfection of NF-κB decoy oligodeoxynucleotides attenuate renal ischemia/reperfusion injury in rats, Kidney International, 2004, 65, pp. 834-845.*
Natarajan Aravindan et al, Fenoldopam Inhibits Nuclear Translocation of Nuclear Factor Kappa B in a Rat Model of Surgical Ischemic Acute Renal Failure, Journal of Cardiothoracic and Vascular Anesthesia, 2006, 20, pp. 179-186.*
International Search Report and Written Opinion dated Feb. 14, 2012 for International Application No. PCT/US2011/056400 (9 pages).
Araujo et al. "Interaction of the Anti-Inflammatory Annexin A1 Protein and Tacrolimus Immunosuppressant in the Renal Function of Rats" *Am J Nephrol* 31:527-533 (2010).
Damazo et al. "Critical Protective Role for Annexin 1 Gene Expression in the Endotoxemic Murine Microcirculation" *Am J Pathol* 166(9):1607-1617 (2005).
Haase et al. "Novel Biomarkers, Oxidative Stress, and the Role of Labile Iron Toxicity in Cardiopulmonary Bypass-Associated Acute Kidney Injury" *J. Am. Coll. Cardiol.* 55:2024-2033 (2010).
La et al. "Annexin 1 Peptides Protect Against Experimental Myocardial Ischemia-Reperfusion: Analysis of Their Mechanism of Action" *FASEB J.* 15:2247-2256 (2001).
Lim et al. "Annexin 1: the New Face of an Old Molecule" *FASEB J.* 21:968-975 (2007).
Rosner et al. "Acute Kidney Injury Associated with Cardiac Surgery" *Clin J Am Soc Nephrol* 1:19-32 (2006).
Zhang et al. "Annexin 1 Induced by Anti-Inflammatory Drugs Binds to NF-κB and Inhibits its Activation: Anticancer Effects In Vitro and In Vivo" 70:2379-2388 (2010).
Notification Concerning Transmittal of International Preliminary Report on Patentability in corresponding PCT Application No. PCT/US2011/056400 mailed Apr. 25, 2013 (7 pages).
Accession No. P04083: ANXA1_HUMAN Nov. 1, 1986 (5 pages).
Augoustides et al. "Major Clinical Outcomes in Adults Undergoing Thoracic Aortic Surgery Requiring Deep Hypothermic Circulatory Arrest: Quantification of Organ-Based Perioperative Outcome and Detection of Opportunities for Perioperative Intervention" *Journal of Cardiothoracic and Vascular Anesthesia* 19(4):446-452 (2005).
Berendsen, Herman J. C. "A Glimpse of the Holy Grail?" *Science* 282:642-643 (1998).
Bizzarro et al. "Annexin A1 N-Terminal Derived Peptide Ac2-26 Stimulates Fibroblast Migration in High Glucose Conditions" *PLoS ONE* 7(9):e45639 (2012).
Bradley et al. "Limits of Cooperativity in a Structurally Modular Protein: Response of the Notch Ankyrin Domain to Analogous Alanine Substitutions in Each Repeat" *Journal of Molecular Biology* 324:373-386 (2002).
Ernst et al. "An Annexin 1 N-Terminal Peptide Activates Leukocytes by Triggering Different Members of the Formyl Peptide Receptor Family" *The Journal of Immunology* 172:7669-7676 (2004).

(Continued)

*Primary Examiner* — Julie Ha
*Assistant Examiner* — Li Ni Komatsu
(74) *Attorney, Agent, or Firm* — Myers Bigel Sibley & Sajovec, P.A.

(57) ABSTRACT

The present invention provides a method of treating, ameliorating and/or preventing cardiac surgery-associated acute kidney injury (AKI) in a subject, comprising administering to the subject a therapeutically effective amount of an annexin A1 (ANXA1) peptide such that the AKI is treated, ameliorated and/or prevented.

2 Claims, 8 Drawing Sheets

(56) References Cited

OTHER PUBLICATIONS

Gastardelo et al. "Functional and Ultrastructural Analysis of Annexin A1 and Its Receptor in Extravasating Neutrophils during Acute Inflammation" *The American Journal of Pathology* 174(1):177-183 (2009).
Gavins et al. "Annexin 1 and Melanocortin Peptide Therapy for Protection Against Ischaemic-Reperfusion Damage in the Heart" *The Scientific World Journal* 6:1008-1023 (2006).
Gavins et al. "Activation of the annexin 1 counter-regulatory circuit affords protection in the mouse brain microcirculation" *The FASEB Journal* 21:1751-1758 (2007).
Hayhoe et al. "Annexin 1 and its bioactive peptide inhibit neutrophil-endothelium interactions under flow: indication of distinct receptor involvement" *Blood* 107:2123-2130 (2006).
Hoffman et al. "Receptor Up-regulation, Internalization, and Interconverting Receptor States" *The Journal of Biological Chemistry* 271(31):18394-18404 (1996).
GenBank Accession No. X05908: "*Homo sapiens* mRNA for lipocortin" Nov. 26, 2008 (2 pages).
International Preliminary Report on Patentability Corresponding to International Application No. PCT/US2010/052884: mailed Apr. 26, 2012.
International Search Report and the Written Opinion of the International Searching Authority Corresponding to International Application No. PCT/US2010/052884: mailed Jan. 10, 2011.
Kamal et al. "An annexin 1 (ANXA1)-derived peptide inhibits prototype antigen-driven human T cell Th1 and Th2 responses in vitro" *Clinical and Experimental Allergy* 31:1116-1125 (2001).
Kosicka-Knox et al. "Ac 2-26, an annexin A1-derived peptide, reduces inflammation in human SGBS adipocytes after hypoxia treatment" *Endocrine Abstracts* 29:P1172 (2012) (Abstract).
Leoni et al. "Annexin A1, formyl peptide receptor, and NOX1 orchestrate epithelial repair" *The Journal of Clinical Investigation* 123(1):443-454 (2013).
Meldrum et al. "Intracellular Signaling Mechanisms of Sex Hormones in Acute Myocardial Inflammation and Injury" *Frontiers in Bioscience* 10:1835-1867 (2005).
Mishra et al. "Amelioration of ischemic acute renal injury by neutrophil gelatinase-associated lipocalin" *Journal of the American Society of Nephrology* 15:3073-3082 (2004).
Movitz et al. "The Annexin I Sequence $Gln^9$—$Ala^{10}$—$Trp^{11}$—$Phe^{12}$ Is a Core Structure for Interaction with the Formyl Peptide Receptor 1" *The Journal of Biological Chemistry* 285(19):14338-14345 (2010).
Ngo et al. "Computational Complexity, Protein Structure Prediction, and the Levinthal Paradox" pp. 491-494 (1994).
Parikh et al. "Urinary IL-18 is an early predictive biomarker of acute kidney injury after cardiac surgery" *Kidney International* 70:199-203 (2006).
Pelzer et al. "17β-Estradiol Prevents Programmed Cell Death in Cardiac Myocytes" *Biochemical and Biophysical Research Communications* 268:192-200 (2000).
Perretti et al. "Involvement of the Receptor for Formylated Peptides in the in Vivo Anti-Migratory Actions of Annexin 1 and its Mimetics" *American Journal of Pathology* 158(6):1969-1973 (2001).
Perretti et al. "Annexin 1: An Endogenous Anti-Inflammatory Protein" *Physiology* 18:60-64 (2003).
Qing et al. "Novel Annexin A1 Tripeptide Ameliorates Acute Kidney Injury after Deep Hypothermic Circulatory Arrest" *ASA Abstracts* Oct. 16, 2010 (Abstract A092) (2 pages).
Ritchie et al. "Cardioprotective actions of an N-terminal fragment of annexin-1 in rat myocardium in vitro" *European Journal of Pharmacology* 461(2-3):171-179 (2003).
Ritchie et al. "Annexin-1 peptide $Anx-1_{2-26}$ protects adult rat cardiac myocytes from cellular injury induced by simulated ischaemia" *British Journal of Pharmacology* 145:495-502 (2005).
Rudinger, J. "Characteristics of the amino acids as components of a peptide hormone sequence" *Peptide Hormones* J. A. Parsons, Ed. (1976) (8 pages).
Sigma "Designing Custom Peptides" Technical Bulletin (2004) (2 pages).
Su et al. "Acute hyperglycemia exacerbates myocardial ischemia/reperfusion injury and blunts cardioprotective effect of GIK" *American Journal of Physiology—Endocrinology and Metabolism* 293:E629-E635 (2007).
Valen et al. "Nuclear Factor Kappa-B and the Heart" *Journal of the American College of Cardiology* 38(2):307-314 (2001).
Voet et al. "Abnormal Hemoglobins" *Biochemistry* Chapter 9.3:235-241 (1995).
Zhai et al. "Effect of estrogen on global myocardial ischemia-reperfusion injury in female rats" *American Journal of Physiology—Heart and Circulatory Physiology* 279:H2766-H2775 (2000).
Zhang et al. "Abstract 3007: Annexin-A1 Mimetic Peptide and PPAR-alpha Agonist Attenuate Hyperglycemic Exacerbation of Myocardial Ischemia/Reperfusion Injury Following Cardioplegic Arrest in the Rat" *Circulation* 120:S731 (2009) (Abstract).
Zhang et al. "A Novel Annexin A1 Peptide Attenuates Perioperative Myocardial Injury Exacerbated by Hyperglycemia" *ASA Abstracts* Oct. 19, 2009 (Abstract A765) (2 pages).
Zhang et al. "Abstract 19839: Annexin-a1 Tripeptide is Cardioprotective in Several Preclinical Models of Ischemia-Reperfusion Through Resolution of Myocardial Inflammation" *AHA Abstracts From Scientific Sessions* 122(21 Supplement) Nov. 13-17, 2010 Chicago, IL (3 pages).
Araujo et al. "Annexin A1 protein attenuates cyclosporine-induced renal hemodynamics changes and macrophage infiltration in rats" *Inflammation Research* 61:189-196 (2012).
Bellomo et al. "Acute renal failure—definition, outcome measures, animal models, fluid therapy and information technology needs: the Second International Consensus Conference of the Acute Dialysis Quality Initiative (ADQI) Group" *Critical Care* 8:R204-R212 (2004).
Daemen et al. "Apoptosis and Inflammation in Renal Reperfusion Injury" *Transplantation* 73(11):1693-1700 (2002).
Facio et al. "Annexin 1 mimetic peptide protects against renal ischemia/reperfusion injury in rats" *Journal of Molecular Medicine* 89:51-63 (2011).
Kourliouros et al. "Low cardiopulmonary bypass perfusion temperatures are associated with acute kidney injury following coronary artery bypass surgery" *European Journal of Cardio-thoracic Surgery* 37:704-709 (2010).
Murphy et al. "An initial evaluation of post-cardiopulmonary bypass acute kidney injury in swine" *European Journal of Cardio-thoracic Surgery* 36:849-855 (2009).
Patel et al. "Phosphodiesterase-5 Inhibition Prevents Postcardiopulmonary Bypass Acute Kidney Injury in Swine" *The Annals of Thoracic Surgery* 92:2168-2176 (2011).
Patel et al. "Prevention of post-cardiopulmonary bypass acute kidney injury by endothelin A receptor blockade" *Critical Care Medicine* 39(4):793-802 (2011).

* cited by examiner

A

B

COMPOSITIONS AND METHODS FOR THE TREATMENT OF CARDIAC SURGERY-ASSOCIATED ACUTE KIDNEY INJURY WITH ANNEXIN A1 PEPTIDE

STATEMENT OF PRIORITY

This application is a 35 U.S.C. §371 national phase application of International Application Serial No. PCT/US2011/056400, filed Oct. 14, 2011, which claims the benefit, under 35 U.S.C. §119(e), of U.S. Provisional Patent Application No. 61/393,402, filed Oct. 15, 2010, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 5405-455_ST25.txt, 11,350 bytes in size, generated on Mar. 24, 2015 and filed via EFS-Web, is provided in lieu of a paper copy. The Sequence Listing is incorporated herein by reference into the specification for its disclosures.

FIELD OF THE INVENTION

The present invention relates to compositions and methods for the treatment of cardiac-surgery-associated acute kidney injury (AKI) using Annexin A1 (ANXA1)-related peptides.

BACKGROUND OF THE INVENTION

Perioperative acute kidney injury (AKI) following major cardiovascular surgery remains a significant problem. Perioperative AKI presents a challenging medical problem occurring in up to 30% of all cardiovascular procedures. The importance of postoperative renal dysfunction comes not only from the acute functional impairment of an organ critical to maintaining the internal environment, but also from its consistent association with increased rates of in-hospital mortality, even after adjustment for other contributing factors. In the setting of deep hypothermic circulatory arrest (DHCA), the incidence ranges as high as 8% to 50% (see, e.g., Augoustides et al. (2005) *J. Cardiothorac. Vasc. Anesth.* 19:446-452). AKI leads to increased postoperative morbidity and mortality, and in patients requiring renal replacement therapy the mortality rate is as high as 64%. However, despite several small "proof-of-concept" clinical studies, to date, there is no promising therapy available for prevention and/or treatment of cardiac surgery-associated AKI. Evidence is cumulating that potential mechanisms are associated with renal inflammation and ischemia-reperfusion (I/R) triggered by cardiopulmonary bypass (CPB) and DHCA.

Annexin A1 (ANXA1), a 37 kDa protein, is a member of the annexin superfamily, which consists of 13 calcium and phospholipid binding proteins with a significant degree of biological and structural homology (40-60%). ANXA1, originally identified as a mediator of the anti-inflammatory affects of glucocorticoids, has diverse biological functions including the regulation of inflammatory pathways, cell proliferation machinery, cell death signaling, and the process of carcinogenesis. Altering the expression or the localization of this protein can contribute to the pathogenesis of human diseases including inflammatory diseases, cardiovascular diseases, and cancer. It has been demonstrated that ANXA1 reduces the leukocyte-dependent myocardial damage associated with myocardial I/R injury (La et al. (2001) *FASEB J.* 15(12):2247-2256). The functional link between migrated leukocytes and the myocardial damage was confirmed, and significantly lower numbers of extravasated leukocytes were counted in the group of rats treated with ANXA1 (La et al., supra). Pharmacological analysis has demonstrated that the first 25 amino acids of the N-terminus of ANXA1 (termed Ac2-26, Ac: aceyl) is the active region of biological function and can reproduce the anti-inflammatory actions of the full-length protein (Gasterdelo et al. (2009) *Am. J Pathol.* 174(1): 177-183). Ac2-26 protects against splanchnic artery occlusion and reperfusion injury by affecting neutrophil migration and against experimental myocardial ischemia-reperfusion by attenuating neutrophil migration (Gasterdelo et al., supra). The role of the endogenous anti-inflammatory mediator ANXA1 in controlling PMN trafficking and activation was addressed using the ANXA1 null mouse. Such findings suggest ANXA1 is a novel anti-inflammatory agent with a potential for the treatment of cardiovascular pathologies associated with neutrophil activation and recruitment. More recently, it has been demonstrated for the first time that ANXA1 N-terminus peptides derived from the N-terminal domain of ANXA1 possess strong anti-inflammatory properties by inhibiting NF-κB activity in human colon and pancreatic cancer cell lines, and in vivo anti-tumorigenesis properties in mice (See, e.g., PCT Publication No. WO/2008/121881).

The present invention provides compositions comprising ANXA1, and methods of using such compositions, for example, for perioperative renoprotection.

SUMMARY OF THE INVENTION

In one aspect, the present invention provides a method of treating, ameliorating and/or preventing cardiac-surgery-associated acute kidney injury (AKI) in a subject (e.g., a subject in need thereof), comprising, consisting of or consisting essentially of administering to the subject a therapeutically effective amount of an ANXA1 peptide such that the AKI is treated, ameliorated and/or prevented.

Another aspect of the present invention provides a kit for the treatment, amelioration and/or prevention of cardiac-surgery-associated acute kidney injury (AKI) in a subject (e.g., a subject in need thereof), comprising, consisting essentially of or consisting of an ANXA1 peptide and instructions for use.

In yet another aspect, the present invention provides the use of an ANXA1 peptide in the manufacture of a medicament for the treatment, prevention and/or amelioration of cardiac-surgery-associated acute kidney injury (AKI) in a subject (e.g., a subject in need thereof).

Another aspect of the present invention provides a composition comprising an ANXA1 peptide in a pharmaceutically acceptable carrier. In particular embodiments, the composition, when administered to a subject, prevents, treats and/or ameliorates cardiac-surgery-associated acute kidney injury (AKI) in the subject.

In some embodiments of this invention, the ANXA1 peptide can comprise, consist essentially of or consist of the amino acid sequence Ac-Gln-Ala-Trp (Ac: aceyl).

The foregoing objects, features and advantages of the present invention will become more apparent from the following description in connection with the accompanying drawings.

DETAILED DESCRIPTION OF THE INVENTION

Figure 1:
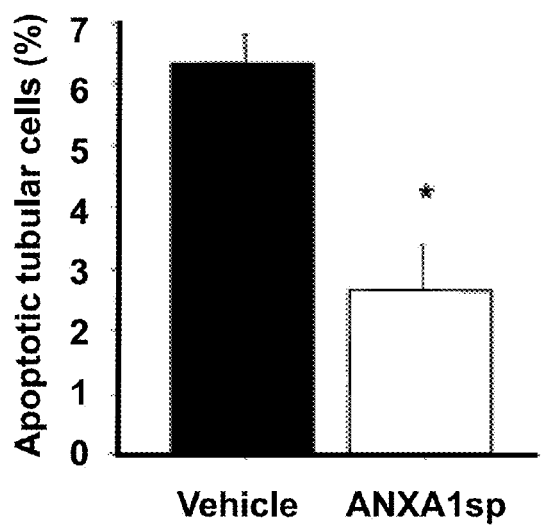
FIG. 1. ANXA1 short peptide (ANXA1sp) treatment ameliorates proximal tubular apoptosis and inhibits the activity of caspase-3 induced by ischemia-reperfusion injury following deep hypothermia circulatory arrest (DHCA). Quantification of apoptosis was determined by terminal deoxynucleotidyl transferase dUTP nick end labeling (TUNEL) staining (Panel A) and the activity of caspase-3 analyzed by Western blot (Panel B) at 24 h after DHCA in rats either treated with ANXA1sp or 0.1% DMSO (vehicle) i.p. Results are shown as mean±SD of six animals in each group. * p<0.002.
Figure 1:
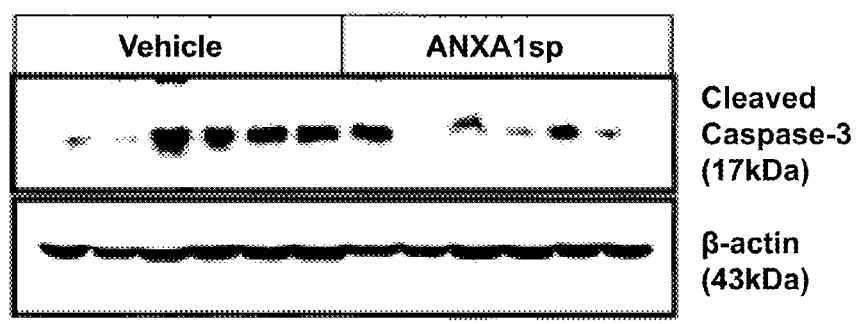

For the purposes of promoting an understanding of the principles of the present invention, reference will now be made to particular embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the invention relates.

The present invention is based on the unexpected discovery that ANXA1 peptide is effective in treating and/or preventing cardiac-surgery-associated acute kidney injury (AKI). Thus, in one embodiment, the present invention provides a method of treating cardiac surgery-associated acute kidney injury in a subject (e.g., a subject in need thereof), comprising, consisting essentially of or consisting of administering to the subject an effective amount of an ANXA1 peptide.

Also provided herein is a method of ameliorating cardiac surgery-associated acute kidney injury (AKI) in a subject (e.g., a subject in need thereof), comprising, consisting essentially of or consisting of administering to the subject an effective amount of an ANXA1 peptide.

In addition the present invention provides a method of preventing cardiac surgery-associated acute kidney injury (AKI) in a subject (e.g., a subject in need thereof), comprising, consisting essentially of or consisting of administering to the subject an effective amount of an ANXA1 peptide.

In some embodiments of this invention, the full length ANXA1 protein can be administered according to the methods described herein, either alone or in combination with one or more of the ANXA1 peptides of this invention and/or in combination with other therapeutic agents as described herein and as would be well known in the art.

In various embodiments of this invention, the ANXA1 peptide can be administered prior to, during and/or after cardiac surgery. Thus, in particular embodiments, the use of the ANXA1sp peptide is planned and anticipated, in comparison with a situation in which a subject has or is at risk of acute kidney injury associated with cardiac surgery that was not planned or anticipated. Furthermore, targeted delivery of an ANXA1 peptide to the myocardium via the coronary circulation can be facilitated by the ability to incorporate the peptide or a composition comprising, consisting essentially of or consisting of the peptide into the cardioplegia solutions routinely administered during cardiac surgical operations.

In further embodiments, the present invention provides a kit for the treatment, amelioration and/or prevention of cardiac surgery-associated acute kidney injury (AKI) in a subject (e.g. a subject in need thereof), comprising an ANXA1 peptide (e.g. a therapeutically effective amount of an ANXA1 peptide) and instructions for use.

Articles "a," "an" and "the" are used herein to refer to one or more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about" when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, rodents (e.g., mice, rats, etc.) and the like. Preferably, the subject is a human patient. In particular embodiments, the subject of this invention is a human subject.

A "subject in need thereof" or "a subject in need of" is a subject known to have, or is suspected of having or developing cardiac surgery-associated acute kidney injury or is at risk of having or developing cardiac surgery-associated acute kidney injury as described herein. In particular embodiments, the subject is in need of, is scheduled for and/or is planning to undergo cardiac surgery (e.g., to treat a cardiac disorder or for cardiac transplantation).

For example, in particular embodiments, a subject of this invention can be administered the peptide of this invention prior to surgery (e.g., prophylactically) to prevent cardiac surgery-associated acute kidney injury. A subject of this invention can also be administered the peptide of this invention during and/or following cardiac surgery to prevent or treat cardiac surgery-associated acute kidney injury.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). In the methods of this invention, the peptide of this invention may be administered alone and/or simultaneously with one or more other compounds. In some embodiments, the compounds may be administered sequentially, in any order. It will be appreciated that the actual method and order of administration will vary according to, inter alia, the particular preparation of compound (s) being utilized, and the particular formulation (s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition such as cardiac-surgery-associated acute kidney injury (AKI). In some embodiments, the term "prevent" refers to the ability to keep a condition such as cardiac-surgery-associated acute kidney injury (AKI) from happening or existing as well as to diminish or delay onset. In some embodiments, the term "treating" refers to the caring for, or dealing with, a condition such as cardiac-surgery-associated acute kidney injury (AKI) either medically or surgically. Also within the scope of the term "treating" is the acting upon a subject with a condition such as cardiac-surgery-associated acute kidney injury (AKI) with an ANXA1 peptide as described herein to improve or alter the condition.

ANXA1 has a molecular weight of about 37 kDa and consists of about 346 amino acids. The amino acid sequence is encoded by nucleotides 75-1115 of GenBank Accession No. X05908 (SEQ ID NO:1) and is known by one skilled in the art as GenBank Accession No. P04083 (SEQ ID NO:2). As used herein, the term "ANXA1 peptides" or "Annexin A1 peptides" are peptide fragments of Annexin A1 (ANXA1), and are shorter than Annexin A1, but have similar biological effects as Annexin A1 on a cell. ANXA1 peptides can optionally be acetylated at the N-terminal amino acid residue. ANXA1 peptides include, but are not limited to, Ac-Gln-Ala-Trp, the peptide Ac-Lys-Gln-Ala-Trp (SEQ ID NO:3); the peptide Ac-Phe-Leu-Lys, the peptide Ac-Phe-Gln-Ala-Trp (SEQ ID NO:4), the peptide Ac-Phe-Leu-Lys-Gln-Ala-Trp (SEQ ID NO:5), the peptide Glu-Phe-Leu-Lys-Gln-Ala-Trp (SEQ ID NO:6), the peptide Phe-Gln-Ala-Trp (SEQ ID NO:4), the peptide Phe-Leu-Lys-Gln-Ala-Trp (SEQ ID NO:5), the peptide Ac-Ala-Met-Val-Ser-Glu-Phe-Leu-Lys-Gln-Ala-Trp (SEQ ID NO:8), the peptide Ala-Met-Val-Ser-Glu-Phe-Leu-Lys-Gln-Ala-Trp (SEQ ID NO:7), the peptide Ac-Val-Ser-Glu-Phe-Leu-Lys-Gln-Ala-Trp (SEQ ID NO:8), Ac-Gln-Ala-Trp-Phe (SEQ ID NO:10), Gln-Ala-Trp-Phe (SEQ ID NO:11) or other fragments of ANXA1 singly or in any combination, as long as they maintain the ANXA1 functionality, such as inhibition of NF-κB proinflammatory pathways. For example, an ANXA1 peptide of this invention can comprise, consist essentially of or consist of any 3, 4, 5, 6, 7, 8, 9, 10, 11, 12, 13, 14, 15, 16, 17, 18, 19, 20, 21, 22, 23, 24, 25, 26, 27, 28, 29, 30, etc. contiguous amino acids of the amino acid sequence of SEQ ID NO:2. Nonlimiting examples include amino acids 1-3, 2-5, 3-6, 4-10, 5-10, 1-10, 5-15, 10-20, 25-30, including any other contiguous amino acid sequence as described herein that may not be explicitly exemplified herein. The production and testing of any such peptides would be carried out according to protocols well known in the art as well as the teachings provided herein.

As used herein, the term "Ac2-26" refers to a 25mer peptide derived from ANXA1 having the sequence Ac-Ala-Met-Val-Ser-Glu-Phe-Leu-Lys-Gln-Ala-Trp-Phe-Ile-Glu-Asn-Glu-Glu-Gln-Glu-Tyr-Val-Gln-Thr-Val-Lys (SEQ ID NO:9).

As used herein, the term "ANXA1sp" or "Annexin A1 short peptide" refers to the 3mer peptide derived from ANXA1 having the sequence Ac-Gln-Ala-Trp.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's *Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

In some embodiments, a unique form of parenteral administration is via direct access to the coronary circulation, added to cardioplegia solutions routinely used during cardiac surgery. Such delivery can follow an antegrade route (via the aortic root into the coronary arteries) and/or a retrograde route (via the coronary sinus, great heart vein).

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

In addition to the ANXA1 peptides provided herein, a composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

Excipients such as diluents increase the bulk of a solid pharmaceutical composition, and may make a pharmaceutical dosage form containing the composition easier for the patient and care giver to handle. Diluents for solid compositions include, but are not limited to, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer (e.g., CARBOPOL®), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, or starch.

The dissolution rate of a compacted solid pharmaceutical composition in the patient's stomach may be increased by the addition of a disintegrant to the composition. Excipients which function as disintegrants include, but are not limited to, alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present disclosure, the active ingredient and any other solid excipients are suspended in a liquid carrier such as water, vegetable oil, alcohol, polyethylene glycol, propylene glycol, or glycerin. As used herein, "active ingredient" means ANXA1 peptides described herein.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present disclosure may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste.

Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the invention, a liquid composition may also contain a buffer such as gluconic acid, lactic acid, citric acid or acetic acid, sodium gluconate, sodium lactate, sodium citrate, or sodium acetate.

Pharmaceutical compositions of the present disclosure discussed above may be useful for inhibiting inflammation to treat, ameliorate and/or prevent cardiac surgery-associated acute kidney injury. "Inhibiting inflammation" in the present invention also means decreasing inflammation, decreasing expression of pro-inflammatory molecules (e.g., NF-κB, and/or decreasing or inhibiting the inflammation cascade to treat ameliorate and/or prevent cardiac surgery-associated acute kidney injury.

The term "administer," "administering" or "administered" as used herein is meant to include topical, parenteral and/or oral administration, all of which are described in herein. By "parenteral" is meant intravenous, subcutaneous or intramuscular administration. In the methods of the present invention, the ANXA1 peptide may be administered alone, simultaneously with one or more other compounds, or the compounds may be administered sequentially, in either order. It will be appreciated that the actual method and order of administration will vary according to, inter cilia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein. The term "administering" or "administered" also refers to oral sublingual, buccal, transnasal, transdermal, rectal, intramascular, intravenous, intraarterial (intracoronary), intraventricular, intrathecal, and subcutaneous routes. In accordance with good clinical practice, it is preferred to administer the instant compounds at a concentration level which will produce effective beneficial effects without causing significant or substantial harmful or untoward side effects. In prophylactic applications, pharmaceutical compositions or medicaments are administered to a subject susceptible to, or otherwise at risk of, suffering cardiac-surgery-associated acute kidney injury (AKI) (e.g., those subjects at risk for heart attack, stroke, myocardial infarction, etc.) in an amount sufficient to eliminate or reduce the risk, lessen the severity, or delay the outset of the injury, including biochemical, histologic and/or physiologic symptoms of the injury. In therapeutic applications, compositions or medicants are administered to a subject suspected of, or already suffering from such an injury in an amount sufficient to treat, or at least partially reduce or arrest, the symptoms of the injury (biochemical, histologic and/or physiological). An amount adequate to accomplish therapeutic or prophylactic treatment is defined as an effective amount or a therapeutically or prophylactically effective dose. In either prophylactic or therapeutic regimens, ANXA1 peptides of the present invention can be and are usually administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the peptides and compositions of this invention will be determined by the age, weight and condition or severity of disease or disorder of the subject.

The amount of ANXA1 peptide can depend on whether additional compounds, such as pharmaceutical carriers, are also administered, with higher dosages being required in the absence of additional compounds. The amount of an ANXA1 peptide for administration according to the methods of this invention can be from about 1 µg to about 500 µg per subject per administration and more usually from about 5 µg to about 500 µg per administration for human administration. In some embodiments, a higher dose of 1-2 mg per administration can be used. Typically about 10, 20, 50 or 100 µg is used for each human administration.

Generally, dosing (e.g., an administration) can be one or more times daily, or less frequently, such as once a day, once a week, once a month, once a year, to once in a decade, etc. and may be in conjunction with other compositions as described herein. In certain embodiments, the dosage is greater than about 1 µg/subject and usually greater than about 10 µg/subject if additional compounds are also administered, and greater than about 10 μg/subject and usually greater than about 100 μg/subject in the absence of additional compounds, such as a pharmaceutical carrier.

An example of a possible dosage regimen may comprise or consist of an initial administration of ANXA1 peptide prior to injury (e.g., prior to or at the beginning of surgery), intraoperative targeted coronary administration with cardioplegia solutions, followed by booster injections at selected time intervals after injury or surgery, such as 1 hour, 1 day or 1 week intervals. Another regimen may consist of an initial intraoperative targeted coronary administration of ANXA1 peptide with cardioplegia solutions, immediately following injury (e.g., surgery) followed by booster injections every 1, 2 and/or 12 hours later. It should be noted that the present invention is not limited to the dosages recited herein.

The dosage and frequency of administration can vary depending on whether the treatment is prophylactic or therapeutic. In prophylactic applications, a relatively low dosage can be administered at relatively infrequent intervals over a long period of time. Some patients may continue to receive treatment for the rest of their lives. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The aforementioned embodiments are not exclusive and may be combined in whole or in part in any combination.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present disclosure is explained in greater detail in the following non-limiting examples.

EXAMPLES

Example I

Figure 2:
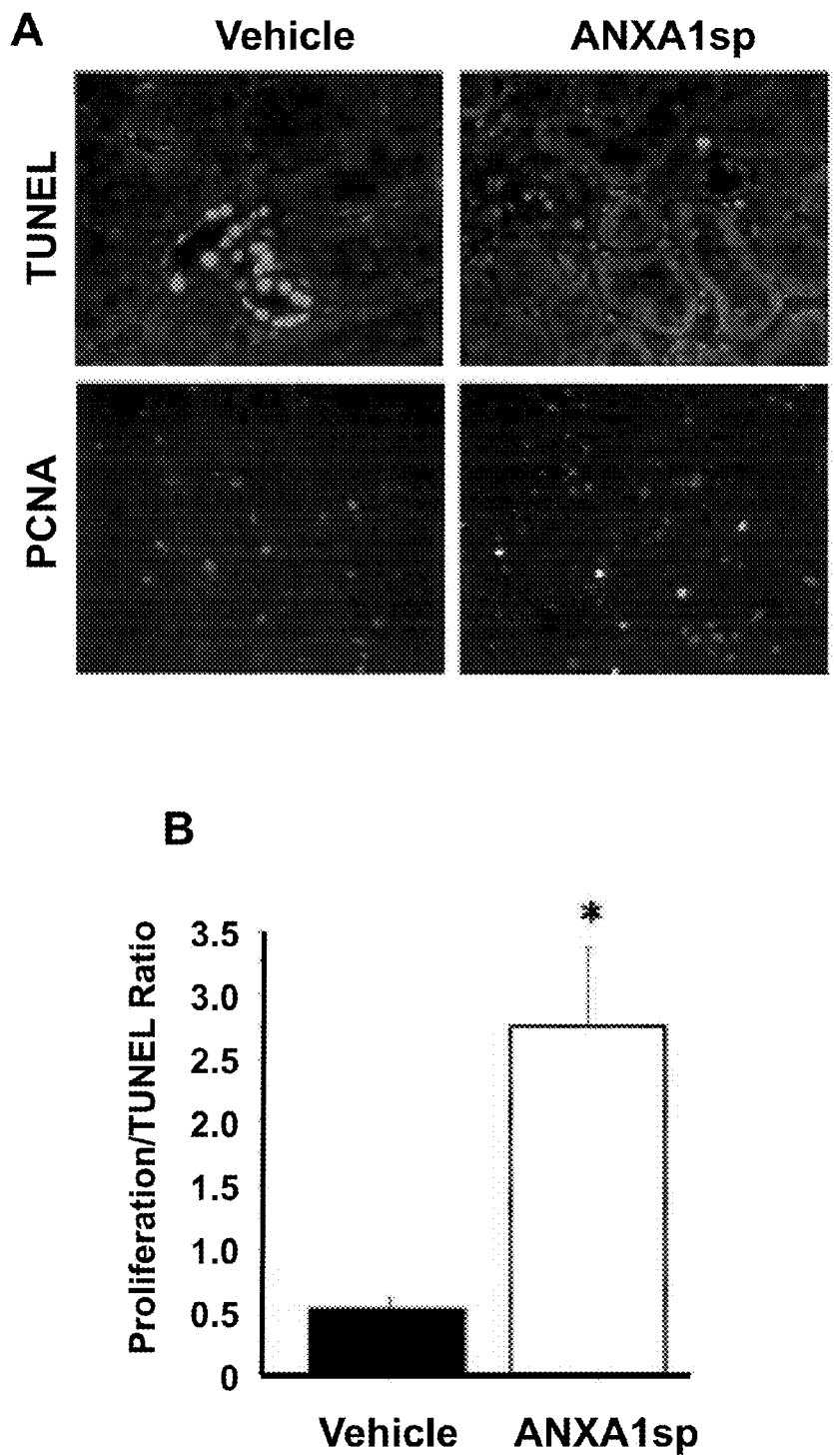
FIG. 2. Effect of treatment of ANXA1sp after ischemia-reperfusion injury on cell apoptosis and cell proliferation. (Panel A) Treatment with ANXA1sp inhibits apoptosis (TUNEL staining) and enhances proliferation (PCNA staining) induced by ischemia-reperfusion injury following deep hypothermia circulatory arrest (DHCA). Representative sections from 24 hrs after DHCA in rats treated with either ANXA1sp or 0.1% DMSO (vehicle) (original magnification 300×). (Panel 13) ANXA1sp tilts the balance of proximal tubular cell fate toward survival after ischemia-reperfusion injury. A ratio of proliferation/apoptosis (TUNEL) was calculated in proximal tubules 24 hrs after DHCA in rats treated with either ANXA1sp or 0.1% DMSO (vehicle). Results were shown as mean±SD of six rats in each group. * p<0.005 versus vehicle.
Figure 3:
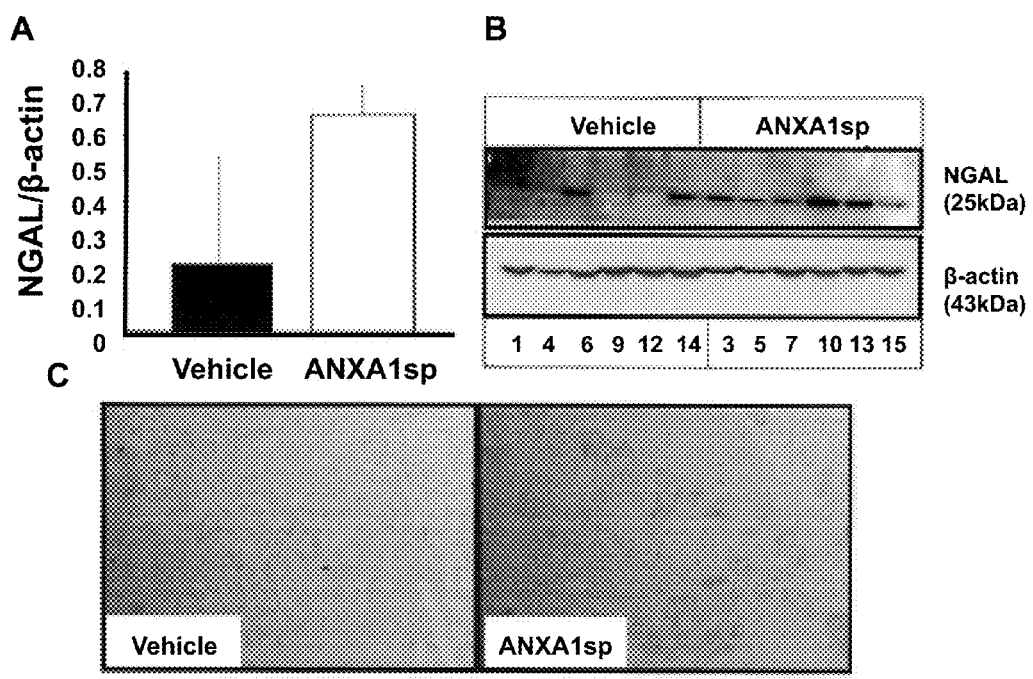
FIG. 3. (Panel A) Protein levels of neutrophil gelatinase associated lipocalin (NGAL) analyzed by Western blot in the kidney 24 hrs after reperfusion following cardiopulmonary bypass (CPB) and deep hypothermic circulatory arrest (DHCA) in vehicle treated animals (Vehicle) versus ANXA1sp treated animals (ANXA1sp). Results are shown as mean±SD. (n=6). *p<0.01 vs. Vehicle. (Panel B) Effect of ANXA1sp on renal NGAL protein levels. Results are representative of six independent experiments in each group. (Panel C) The location of NGAL protein detected by immunohistochemistry in the kidney 24 hrs after reperfusion following DHCA in vehicle treated animals (Vehicle) versus ANXA1sp treated animals (ANXA1sp). NGAL protein was visualized with the NGAL antibody. NGAL positive staining was abundant in ANXA1sp treated animals and mainly located in the proximal tubule cells (original magnification 200×).
Figure 4:
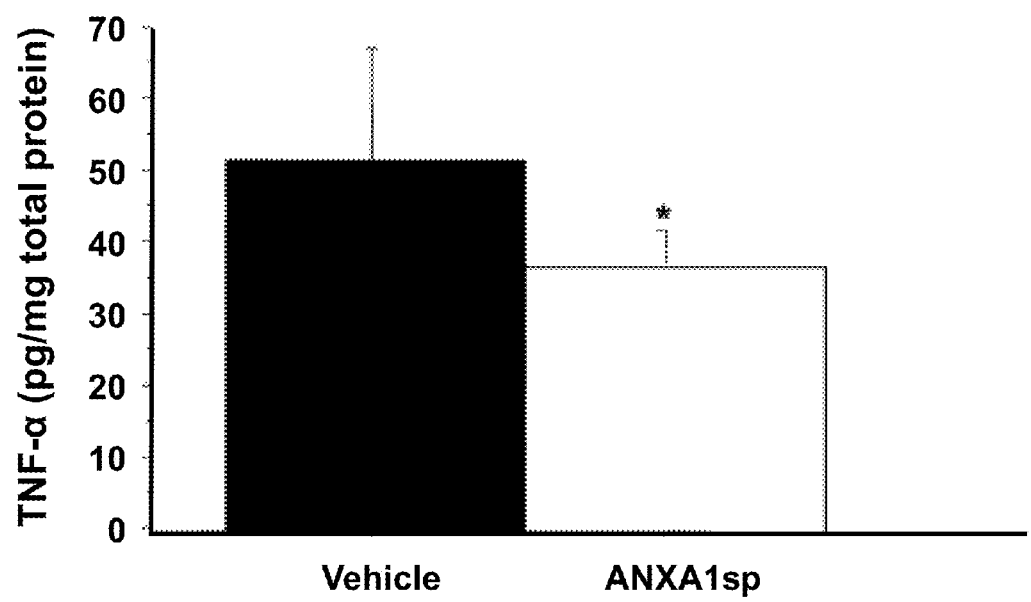
FIG. 4. ANXA1sp treatment represses the renal levels of TNF-α induced by ischemia-reperfusion injury following deep hypothermia circulatory arrest (DHCA) analyzed by ELISA in the kidney 24 hrs after reperfusion in rats either treated with ANXA1sp (open bar, n=6) or vehicle (0.1% DMSO) i.p. (filled bar, n=6). Results are expressed as mean value±SD; * p<0.05 vs. Vehicle.
Figure 5:
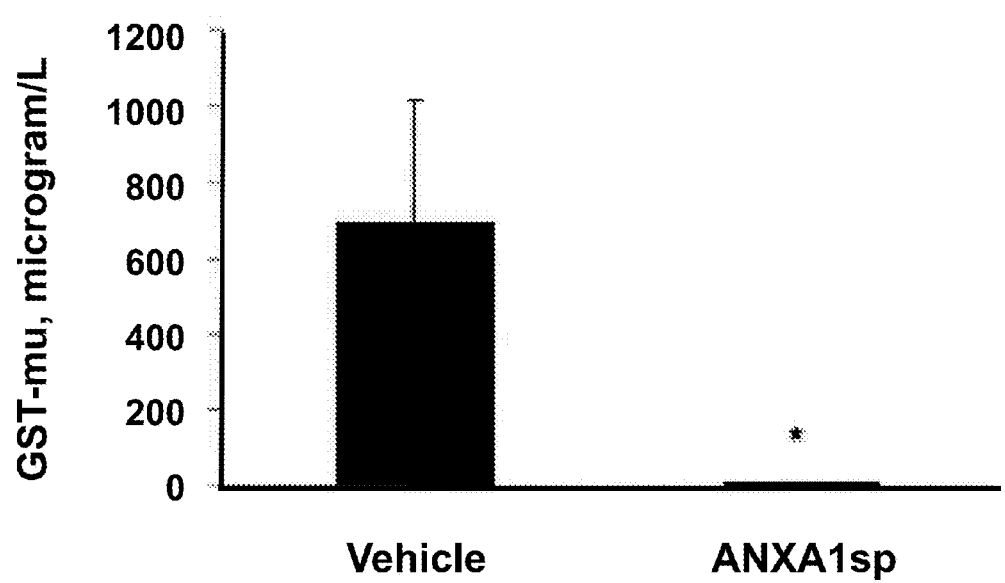
FIG. 5. ANXA1sp significantly attenuates AKI, as evidenced by reduced expression of early renal biomarker GST-μ in rat urine in a preclinical model of CPB/CA. Values presented are means±SD; n=3; * p<0.05 vs. Vehicle.

Using translation approaches, previous experiments by the inventors have shown that a novel ANXA1 tripeptide (ANXA1sp) derived from the N-terminal domain has robust cardioprotective efficacy in several in vitro and in vivo preclinical models of myocardial ischemia-reperfusion (see, e.g., PCT Publication No. WO 2011/047290; Zhang et al. Circulation 120:S731 (2009). In the present invention it is shown that ANXA1sp significantly attenuates cardiac-surgery associated acute kidney injury (AKI) in a preclinical rat model of CPB/DHCA. As shown in FIG. 1, animals treated with ANXA1sp showed reduced numbers of proximal tubular cells (FIG. 1, Panel A) and lower activity of caspase-3 compared to vehicle (FIG. 1, Panel B). Treatment with ANXA1sp also enhanced tubule cell proliferation and tilted the balance of proximal tubular cell fate toward survival after ischemia-reperfusion injury (FIG. 2, Panels A and B). Rats treated with ANXA1sp showed a significantly higher expression of Neutrophil Gelatinase-Associated Lipocalin (NGAL—which participates in local iron transport) in the kidney compared to vehicle (FIG. 3, Panels A and B). NGAL positive staining was abundant in ANXA1sp treated animals and mainly located in the proximal tubule cells (FIG. 3, Panel C). Rats treated with ANXA1sp showed significantly lower levels of proinflammatory cytokine TNF-α protein in the kidney as compared to vehicle (FIG. 4). In addition, ANXA1sp significantly attenuated perioperative AKI as evidenced by significantly reduced expression of the early renal biomarker, g-class glutathione S transferase (GST-μ) in rat urine in a setting of myocardial ischemia/reperfusion (FIG. 5).

These results provide evidence for the renoprotective efficacy of ANXA1sp in the setting of AKI using a clinically relevant animal model of CPB and DHCA. The beneficial effect of ANXA1sp may be associated with an increased production in renal NGAL in response to AKI. The ANXA1sp tilts the balance of proximal tubular cell fate towards survival.

These findings will facilitate first-in-human studies for ANXA1sp to reduce perioperative AKI in patients undergoing major cardiovascular surgery. This novel short peptide may be a potential agent/therapy for not only perioperative cardioprotection but also perioperative renoprotection.

The compositions and methods provided herein show clinical renal marker-based amelioration of cardiac-surgery associated AKI and identify novel strategies for the management of AKI under cardiac therapy. ANXA1sp provides a novel approach to controlling inflammation with cardiac surgery-associated AKI without the significant toxicity and side effects associated with currently available anti-inflammatory compounds such as corticosteroids and non-steroidal anti-inflammatory drugs.

Example II

Acute kidney injury (AKI) after aortic arch surgery is common and is associated with a significant increase in morbidity and mortality. Renal and systemic inflammation introduced by cardiopulmonary bypass (CPB) and deep hypothermic circulatory arrest (DHCA) are considered to play a key role in mediating AKI. Annexin-A1 (ANXA1), an endogenous protein, has strong anti-inflammatory properties. Using a number of preclinical models, it has been demonstrated that an ANXA1 tripeptide (ANXA1sp) provides robust anti-inflammatory actions and organ-protective properties. Studies described herein were conducted to demonstrate that ANXA1sp is renoprotective and modulates renal inflammation by reducing NF-kappa B activation following cardiopulmonary bypass (CPB)/deep hypothermic circulatory arrest (DHCA).

Male Sprague-Dawley rats were prepared for 60 min of DHCA at 18° C. and received either vehicle or ANXA1sp (2 mg/kg) i.v. at one hour before CPB and one hour after reperfusion. Renal tissue and serum samples were harvested at 3 (n=5), 6 (n=3), and 24 hours (n=3) i.v. after CPB/DHCA. The time course of renal activity of NF-kappa B was determined by a rat specific ELISA kit. Changes of renal and serum levels of the proinflammatory cytokines tumor necrosis factor-alpha (TNF-α) and interleukin (IL)-6 as well as myeloperoxidase (MPO) were measured by ELISA. Changes of renal levels of activated caspase-3 were determined by Western blot. At 24 hours after DHCA, apoptotic proximal tubular cells was identified by TUNEL and quantified by counting the numbers of apoptotic proximal tubular cells in 5 representative renal areas.

Figure 6:
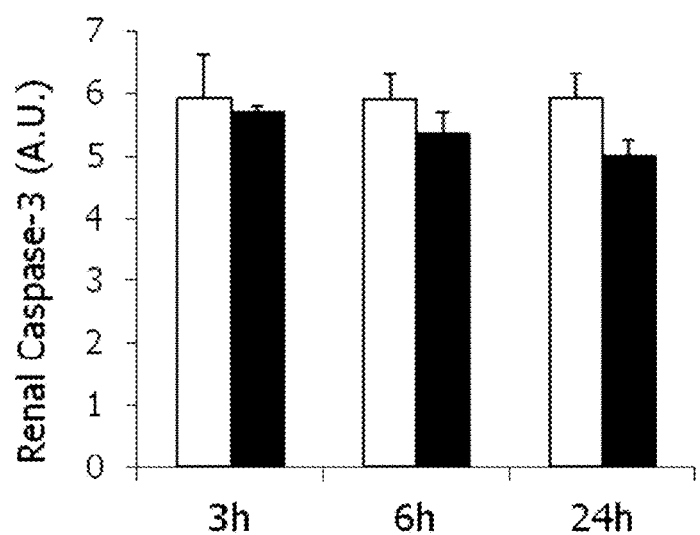
FIG. 6. Annexin-A1 short peptide (ANXA1sp) treatment ameliorates proximal tubular apoptosis and inhibits the activity of caspase-3 induced by ischemia-reperfusion injury following deep hypothermia circulatory arrest (DHCA). The activity of caspase-3 analyzed by Western blot (Panel A) at different time points and quantification of apoptosis was determined by TUNEL staining (Panel B) at 24 h after DHCA in rats either treated with AXNA1 sp or 0.1% DMSO (vehicle) iv. Results are shown as means±SD. * p<0.05 vs. vehicle.
Figure 6:
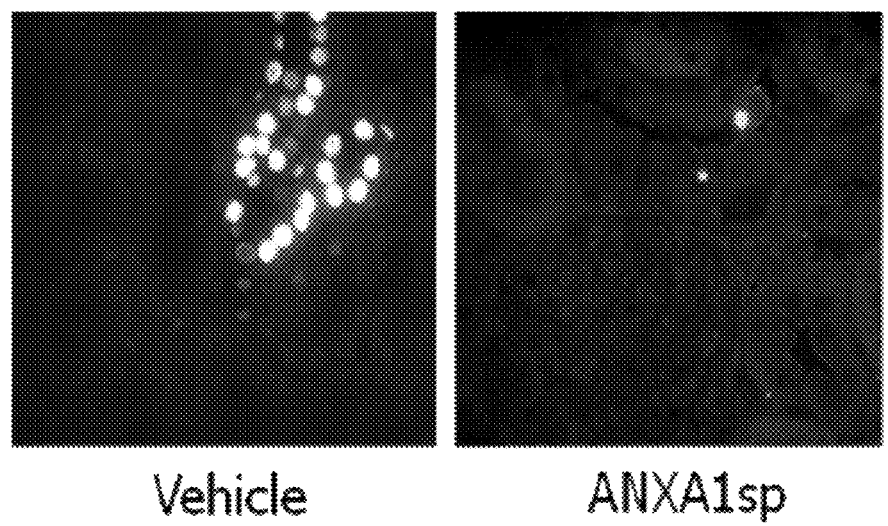

ANXA1sp significantly decreased renal activity of caspase-3 (FIG. 6, Panel A) and reduced numbers of apoptotic proximal tubular cells (FIG. 6, Panel B) compared to vehicle.

Figure 7:
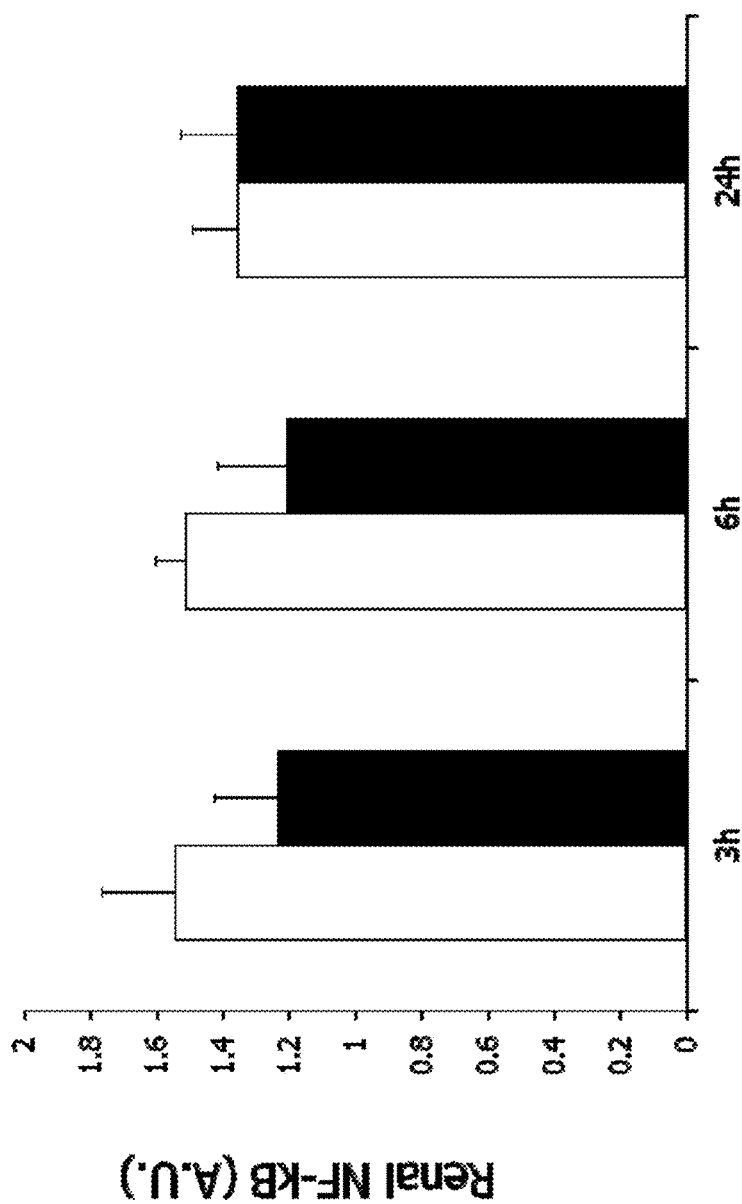
FIG. 7. Administration of Annexin-A1 short peptide (ANXA1sp) significantly inhibits the renal activity of NF-kappa 13 at 3 and 6 hours after deep hypothermia circulatory arrest (DHCA) in rats treated either with ANXA1sp or 0.1% DMSO (vehicle). Results are shown as means±SD. * p<0.05 vs. vehicle.

Animals treated with ANXA1sp showed significant inhibition of renal activity of NF-kappa B early stages after CPB/DHCA (FIG. 7).

Figure 8:
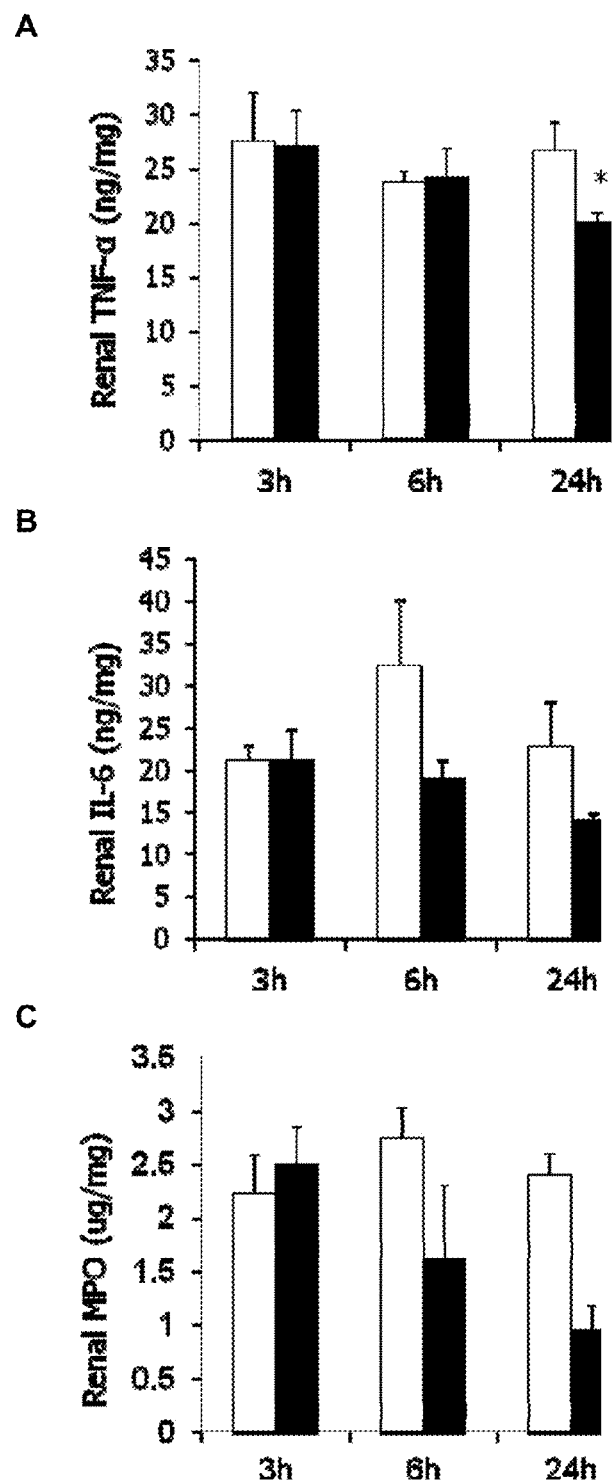
FIG. 8. Annexin-A1 short peptide (ANXA1sp) treatment significantly decreases renal levels of pro-inflammatory cytokines TNF-α (Panel A) at 24 hours and IL-6 (Panel B) as well as MPO (Panel C) either at 6 and 24 after deep hypothermic circulatory arrest (DHCA) in rats either treated with AXNA1sp or 0.1% DMSO (vehicle) iv. Results are shown as Means±SD. * p<0.05 vs. vehicle.

ANXA1sp significantly suppressed renal levels of pro-inflammatory cytokines TNF-α (FIG. 8, Panel A) and IL-6 (FIG. 8, Panel B) as well as MPO (FIG. 8, Panel C) following CPB/DHCA. ANXA1sp significantly reduced release of TNF-α, IL-6 and MPO in the serum compared to vehicle (data not shown).

This study provides evidence that administration of ANXA1sp attenuates AKI following CPB/DHCA. The beneficial effect of ANXA1sp may be associated with inhibiting renal activity of NF-kappa B, suppressing the release of pro-inflammatory cytokines well as neutrophil transmigration.

Variations and modifications of the herein described systems, apparatuses, methods and other applications will undoubtedly suggest themselves to those skilled in the art. Accordingly, the foregoing description should be taken as illustrative and not in a limiting sense.

Any patents, publications, sequences and other references mentioned in this specification are indicative of the levels of those skilled in the art to which the invention pertains. These patents, publications, sequences and references are incorporated by reference herein to the same extent as if each was specifically and individually indicated to be incorporated by reference herein.

We claim:

1. A method of treating acute kidney injury (AKI) due to cardiac surgery or cardiac transplantation in a subject having cardiac surgery or cardiac transplantation, comprising administering to said subject an effective amount of an annexin A1 short peptide (ANXA1sp) consisting of the amino acid sequence Ac-Gln-Ala-Trp, wherein the ANXA1sp is administered to the subject prior to, during and/or after cardiac surgery or cardiac transplantation, thereby treating AKI due to cardiac surgery or cardiac transplantation.

2. A method of ameliorating acute kidney injury (AKI) due to cardiac surgery or cardiac transplantation in a subject having cardiac surgery or cardiac transplantation, comprising administering to said subject an effective amount of an annexin A1 short peptide (ANXA1sp) consisting of the amino acid sequence Ac-Gln-Ala-Trp, wherein the ANXA1sp is administered to the subject prior to, during and/or after cardiac surgery or cardiac transplantation, thereby ameliorating AKI due to cardiac surgery or cardiac transplantation.

* * * * *

UNITED STATES PATENT AND TRADEMARK OFFICE
CERTIFICATE OF CORRECTION

| | |
|---|---|
| PATENT NO. | : 9,173,918 B2 |
| APPLICATION NO. | : 13/879558 |
| DATED | : November 3, 2015 |
| INVENTOR(S) | : Zhang et al. |

It is certified that error appears in the above-identified patent and that said Letters Patent is hereby corrected as shown below:

IN THE SPECIFICATION

Column 3, Line 64: Delete "kappa 13" Insert -- kappa B --

Column 10, Line 18: Insert
          -- effects.
In prophylactic applications, pharmaceuti- --

Column 12, Line 4: Delete "g-class" Insert -- μ-class --

Signed and Sealed this
Twelfth Day of April, 2016

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 1399
<212> TYPE: DNA
<213> ORGANISM: Homo sapiens
<220> FEATURE:
<221> NAME/KEY: CDS
<222> LOCATION: (75)..(1115)

<400> SEQUENCE: 1
agtgtgaaat cttcagagaa gaatttctct ttagttcttt gcaagaaggt agagataaag      60 acacttttc aaaa atg gca atg gta tca gaa ttc ctc aag cag gcc tgg        110
              Met Ala Met Val Ser Glu Phe Leu Lys Gln Ala Trp
                1               5                   10 ttt att gaa aat gaa gag cag gaa tat gtt caa act gtg aag tca tcc       158
Phe Ile Glu Asn Glu Glu Gln Glu Tyr Val Gln Thr Val Lys Ser Ser
             15                  20                  25 aaa ggt ggt ccc gga tca gcg gtg agc ccc tat cct acc ttc aat cca       206
Lys Gly Gly Pro Gly Ser Ala Val Ser Pro Tyr Pro Thr Phe Asn Pro
     30                  35                  40 tcc tcg gat gtc gct gcc ttg cat aag gcc ata atg gtt aaa ggt gtg       254
Ser Ser Asp Val Ala Ala Leu His Lys Ala Ile Met Val Lys Gly Val
 45                  50                  55                  60 gat gaa gca acc atc att gac att cta act aag cga aac aat gca cag       302
Asp Glu Ala Thr Ile Ile Asp Ile Leu Thr Lys Arg Asn Asn Ala Gln
                 65                  70                  75 cgt caa cag atc aaa gca gca tat ctc cag gaa aca gga aag ccc ctg       350
Arg Gln Gln Ile Lys Ala Ala Tyr Leu Gln Glu Thr Gly Lys Pro Leu
             80                  85                  90 gat gaa aca ctt aag aaa gcc ctt aca ggt cac ctt gag gag gtt gtt       398
Asp Glu Thr Leu Lys Lys Ala Leu Thr Gly His Leu Glu Glu Val Val
         95                 100                 105 tta gct ctg cta aaa act cca gcg caa ttt gat gct gat gaa ctt cgt       446
Leu Ala Leu Leu Lys Thr Pro Ala Gln Phe Asp Ala Asp Glu Leu Arg
    110                 115                 120 gct gcc atg aag ggc ctt gga act gat gaa gat act cta att gag att       494
Ala Ala Met Lys Gly Leu Gly Thr Asp Glu Asp Thr Leu Ile Glu Ile
125                 130                 135                 140 ttg gca tca aga act aac aaa gaa atc aga gac att aac agg gtc tac       542
Leu Ala Ser Arg Thr Asn Lys Glu Ile Arg Asp Ile Asn Arg Val Tyr
                145                 150                 155 aga gag gaa ctg aag aga gat ctg gcc aaa gac ata acc tca gac aca       590
Arg Glu Glu Leu Lys Arg Asp Leu Ala Lys Asp Ile Thr Ser Asp Thr
            160                 165                 170 tct gga gat ttt cgg aac gct ttg ctt tct ctt gct aag ggt gac cga       638
Ser Gly Asp Phe Arg Asn Ala Leu Leu Ser Leu Ala Lys Gly Asp Arg
        175                 180                 185
```

| | | |
|---|---|---|
| tct gag gac ttt ggt gtg aat gaa gac ttg gct gat tca gat gcc agg<br>Ser Glu Asp Phe Gly Val Asn Glu Asp Leu Ala Asp Ser Asp Ala Arg<br>190                       195                      200 | | 686 |
| gcc ttg tat gaa gca gga gaa agg aga aag ggg aca gac gta aac gtg<br>Ala Leu Tyr Glu Ala Gly Glu Arg Arg Lys Gly Thr Asp Val Asn Val<br>205                       210                     215                  220 | | 734 |
| ttc aat acc atc ctt acc acc aga agc tat cca caa ctt cgc aga gtg<br>Phe Asn Thr Ile Leu Thr Thr Arg Ser Tyr Pro Gln Leu Arg Arg Val<br>                     225                       230                     235 | | 782 |
| ttt cag aaa tac acc aag tac agt aag cat gac atg aac aaa gtt ctg<br>Phe Gln Lys Tyr Thr Lys Tyr Ser Lys His Asp Met Asn Lys Val Leu<br>                     240                       245                     250 | | 830 |
| gac ctg gag ttg aaa ggt gac att gag aaa tgc ctc aca gct atc gtg<br>Asp Leu Glu Leu Lys Gly Asp Ile Glu Lys Cys Leu Thr Ala Ile Val<br>255                       260                     265 | | 878 |
| aag tgc gcc aca agc aaa cca gct ttc ttt gca gag aag ctt cat caa<br>Lys Cys Ala Thr Ser Lys Pro Ala Phe Phe Ala Glu Lys Leu His Gln<br>270                       275                     280 | | 926 |
| gcc atg aaa ggt gtt gga act cgc cat aag gca ttg atc agg att atg<br>Ala Met Lys Gly Val Gly Thr Arg His Lys Ala Leu Ile Arg Ile Met<br>285                       290                     295                  300 | | 974 |
| gtt tcc cgt tct gaa att gac atg aat gat atc aaa gca ttc tat cag<br>Val Ser Arg Ser Glu Ile Asp Met Asn Asp Ile Lys Ala Phe Tyr Gln<br>                     305                       310                     315 | | 1022 |
| aag atg tat ggt atc tcc ctt tgc caa gcc atc ctg gat gaa acc aaa<br>Lys Met Tyr Gly Ile Ser Leu Cys Gln Ala Ile Leu Asp Glu Thr Lys<br>                     320                       325                     330 | | 1070 |
| gga gat tat gag aaa atc ctg gtg gct ctt tgt gga gga aac taa<br>Gly Asp Tyr Glu Lys Ile Leu Val Ala Leu Cys Gly Gly Asn<br>335                       340                     345 | | 1115 |
| acattccctt gatggtctca agctatgatc agaagacttt aattatatat tttcatccta | | 1175 |
| taagcttaaa taggaaagtt tcttcaacag gattacagtg tagctaccta catgctgaaa | | 1235 |
| aatatagcct ttaaatcatt tttatattat aactctgtat aatagagata agtccatttt | | 1295 |
| ttaaaaatgt tttccccaaa ccataaaacc ctatacaagt tgttctagta acaatacatg | | 1355 |
| agaaagatgt ctatgtagct gaaaataaaa tgacgtcaca agac | | 1399 |

<210> SEQ ID NO 2
<211> LENGTH: 346
<212> TYPE: PRT
<213> ORGANISM: Homo sapiens

<400> SEQUENCE: 2

Met Ala Met Val Ser Glu Phe Leu Lys Gln Ala Trp Phe Ile Glu Asn
1               5                    10                   15

Glu Glu Gln Glu Tyr Val Gln Thr Val Lys Ser Ser Lys Gly Gly Pro
               20                   25                   30

Gly Ser Ala Val Ser Pro Tyr Pro Thr Phe Asn Pro Ser Ser Asp Val
               35                   40                   45

Ala Ala Leu His Lys Ala Ile Met Val Lys Gly Val Asp Glu Ala Thr
      50                   55                   60

Ile Ile Asp Ile Leu Thr Lys Arg Asn Asn Ala Gln Arg Gln Gln Ile
65               70                   75                   80

Lys Ala Ala Tyr Leu Gln Glu Thr Gly Lys Pro Leu Asp Glu Thr Leu
               85                   90                   95

Lys Lys Ala Leu Thr Gly His Leu Glu Glu Val Val Leu Ala Leu Leu
              100                   105                  110

```
Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Ser Gly Asp Phe
                165                 170                 175

Arg Asn Ala Leu Leu Ser Leu Ala Lys Gly Asp Arg Ser Glu Asp Phe
                180                 185                 190

Gly Val Asn Glu Asp Leu Ala Asp Ser Asp Ala Arg Ala Leu Tyr Glu
                195                 200                 205

Ala Gly Glu Arg Arg Lys Gly Thr Asp Val Asn Val Phe Asn Thr Ile
            210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
                260                 265                 270

Ser Lys Pro Ala Phe Phe Ala Glu Lys Leu His Gln Ala Met Lys Gly
            275                 280                 285

Val Gly Thr Arg His Lys Ala Leu Ile Arg Ile Met Val Ser Arg Ser
            290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
                340                 345

<210> SEQ ID NO 3
<211> LENGTH: 4
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

<400> SEQUENCE: 3

Lys Gln Ala Trp
1

<210> SEQ ID NO 4
<211> LENGTH: 4
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is optionally acetylated

<400> SEQUENCE: 4

Phe Gln Ala Trp
1
```

<210> SEQ ID NO 5
<211> LENGTH: 6
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is optionally acetylated

<400> SEQUENCE: 5

Phe Leu Lys Gln Ala Trp
1               5

<210> SEQ ID NO 6
<211> LENGTH: 7
<212> TYPE: PRT
<213> ORGANISM: Artificial
<220> FEATURE:
<223> OTHER INFORMATION: Synthetic ANXA1 peptide

<400> SEQUENCE: 6

Glu Phe Leu Lys Gln Ala Trp
1               5

<210> SEQ ID NO 7
<211> LENGTH: 11
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is optionally acetylated

<400> SEQUENCE: 7

Ala Met Val Ser Glu Phe Leu Lys Gln Ala Trp
1               5                   10

<210> SEQ ID NO 8
<211> LENGTH: 9
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

<400> SEQUENCE: 8

Val Ser Glu Phe Leu Lys Gln Ala Trp
1               5

<210> SEQ ID NO 9
<211> LENGTH: 25
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

```
<400> SEQUENCE: 9

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 10
<211> LENGTH: 4
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

<400> SEQUENCE: 10

Gln Ala Trp Phe
1

<210> SEQ ID NO 11
<211> LENGTH: 4
<212> TYPE: PRT
<213> ORGANISM: Artificial
<220> FEATURE:
<223> OTHER INFORMATION: Synthetic ANXA1 peptide

<400> SEQUENCE: 11

Gln Ala Trp Phe
1
```